(12) United States Patent
Elphick et al.

(10) Patent No.: US 8,945,626 B2
(45) Date of Patent: *Feb. 3, 2015

(54) PREPARATION OF PHARMACEUTICAL COMPOSITIONS

(76) Inventors: Andrew James Elphick, Long Hanborough (GB); John Staniforth, Chippenham (GB); Dong Wang, Prenton (GB); David John Duncalf, Little Neston (GB); Steven Paul Rannard, Mickle Trafford (GB); James Long, Oxton (GB); Alison Jayne Foster, Higher Bebington (GB)

( * ) Notice: Subject to any disclaimer, the term of this patent is extended or adjusted under 35 U.S.C. 154(b) by 1002 days.

This patent is subject to a terminal disclaimer.

(21) Appl. No.: 12/309,344

(22) PCT Filed: Jul. 13, 2007

(86) PCT No.: PCT/GB2007/050407
§ 371 (c)(1),
(2), (4) Date: Aug. 24, 2009

(87) PCT Pub. No.: WO2008/007150
PCT Pub. Date: Jan. 17, 2008

(65) Prior Publication Data
US 2010/0068282 A1    Mar. 18, 2010

(30) Foreign Application Priority Data
Jul. 13, 2006   (GB) .................................. 0613925.7
Jun. 29, 2007   (WO) ................ PCT/EP2007/056560

(51) Int. Cl.
*A61K 9/14*      (2006.01)
*A61K 8/81*      (2006.01)
*A61K 31/167*    (2006.01)
*A61K 9/16*      (2006.01)
*A01N 25/04*     (2006.01)
*A61K 9/10*      (2006.01)
*A61K 9/19*      (2006.01)

(52) U.S. Cl.
CPC ............. *A61K 9/1617* (2013.01); *A61K 31/167* (2013.01); *A01N 25/04* (2013.01); *A61K 9/10* (2013.01); *A61K 9/1635* (2013.01); *A61K 9/1652* (2013.01); *A61K 9/19* (2013.01)
USPC ........ 424/489; 424/70.15; 424/409; 514/338; 514/630

(58) Field of Classification Search
None
See application file for complete search history.

(56) References Cited

U.S. PATENT DOCUMENTS

| | | |
|---|---|---|
| 4,719,146 A | 1/1988 | Hohage et al. |
| 6,207,674 B1 | 3/2001 | Smith |
| 6,395,300 B1 * | 5/2002 | Straub et al. .................. 424/489 |
| 6,645,528 B1 | 11/2003 | Straub et al. |
| 6,932,983 B1 | 8/2005 | Straub et al. |
| 7,691,873 B2 * | 4/2010 | Duncalf et al. ............... 514/282 |
| 2002/0041896 A1 | 4/2002 | Straub et al. |
| 2002/0142050 A1 | 10/2002 | Straub et al. |
| 2004/0180089 A1 | 9/2004 | Plachetka et al. |
| 2004/0197301 A1 * | 10/2004 | Zhao et al. .................. 424/78.26 |
| 2005/0048116 A1 | 3/2005 | Straub et al. |
| 2005/0058710 A1 | 3/2005 | Straub et al. |
| 2006/0105038 A1 | 5/2006 | Lai et al. |
| 2007/0081947 A1 | 4/2007 | Eble et al. |

FOREIGN PATENT DOCUMENTS

| | | | |
|---|---|---|---|
| EP | 1 598 066 A1 | 11/2005 | |
| JP | 2005298347 | 10/2005 | |
| WO | WO97/13503 | * 4/1997 | ............... A61K 9/16 |
| WO | WO 97/13503 A1 | 4/1997 | |
| WO | WO 97/35562 A1 | 10/1997 | |
| WO | WO 97/38678 A1 | 10/1997 | |
| WO | 98/29098 | 7/1998 | |
| WO | 00/72827 A2 | 12/2000 | |
| WO | WO 00/72827 A2 | 12/2000 | |
| WO | WO 01/00243 A1 | 1/2001 | |
| WO | WO 01/13889 A1 | 3/2001 | |
| WO | WO 01/39836 A1 | 6/2001 | |
| WO | WO 01/89484 A2 | 11/2001 | |
| WO | WO 02/03955 A1 | 1/2002 | |
| WO | WO 02/098352 | 12/2002 | |
| WO | 03026611 | 4/2003 | |
| WO | WO 2004/091665 A1 | 10/2004 | |
| WO | 2005011636 | 2/2005 | |
| WO | WO 2005/117837 A1 | 12/2005 | |
| WO | 2006000383 | 1/2006 | |

OTHER PUBLICATIONS

Powder definition from "audioenglish.org" (last visit, Feb. 11, 2014).*
Surfactant: the ubiquitous amphiphiles, Royal Society of Chemistry, pp. 1-7 (2003) [retrieved on Jun. 26, 2014 from on line website (http://www.rsc.org/chemistryworld/issues/2003/july/amphiphiles.asp)].*
Palmieri et al. (2001) "Spray-drying as a method for microparticulate controlled release systems preparation: advantages and limits. I. Water-soluable drugs." *Drug Development and Industrial Pharmacy*, 27(3): 195-204.
Raffa (2001) "Pharmacology of oral combination analgesics: Rational therapy for pain." *Journal of Clinical Pharmacy and Therapeutics*, 26(4): 257-264.

(Continued)

*Primary Examiner* — Ernst V Arnold
*Assistant Examiner* — Kyung Sook Chang
(74) *Attorney, Agent, or Firm* — Michael Best & Friedrich LLP

(57) ABSTRACT

A process for the production of a composition comprising a water-insoluble paracetamol or NSAID which comprises the steps of: a) providing a mixture comprising: i) a water-insoluble paracetamol or NSAID, ii) a water soluble carrier, and iii) a solvent for each of the paracetamol or NSAID and the carrier, and b) spray-drying the mixture to remove the or each solvent and obtain a substantially solvent-free nano-dispersion of the paracetamol or NSAID in the carrier.

5 Claims, No Drawings

(56) References Cited

OTHER PUBLICATIONS

Vermeire and Remon (1999) "Compatibility and stability of ternary admixtures of morphine with haloperidol or midazolam and dexamethasone or methylprednisolone." *International Journal of Pharmaceutics*, 177(1): 53-67.

Weuts et al. (2005) "Study of the physicochemical properties and stability of solid dispersions of loperamide and PEG6000 prepared by spray drying." *European Journal of Pharmaceutics and Biopharmaceutics*, 59(1): 119-126.

Pursuant to MPEP § 2001.6(b) applicants bring the following co-pending application to the Examiner's attention: Applicant: Cooper, et al, U.S. Appl. No. 10/587,734, filed May 17, 2007, For: Porous Bodies & Method of Production Thereof.

Pursuant to MPEP § 2001.6(b) applicants bring the following co-pending application to the Examiner's attention: Applicant: Barnwell, et al., U.S. Appl. No. 11/883,215, filed May 27, 2007, For: Spray Dried Composition.

Pursuant to MPEP § 2001.6(b) applicants bring the following co-pending application to the Examiner's attention: Applicant: Cooper, et al., U.S. Appl. No. 11/883,216, filed May 27, 2007, For: Method of Preparing Carrier Liquids.

Pursuant to MPEP § 2001.6(b) applicants bring the following co-pending application to the Examiner's attention: Applicant: Cooper, et al., U.S. Appl. No. 10/587,732, filed May 17, 2007, For: Porous Bodies & Method of Production Thereof.

Pursuant to MPEP § 2001.6(b) applicants bring the following co-pending application to the Examiner's attention: Applicant: Butler, et al., U.S. Appl. No. 10/566,873, filed Jul. 3, 2006, For: Porous Material & Method of Production Thereof.

Pursuant to MPEP § 2001.6(b) applicants bring the following co-pending application to the Examiner's attention: Applicant: Angus, et al., U.S. Appl. No. 12/309,306, filed Jan. 13, 2009, For: Nanodispersions.

Pursuant to MPEP § 2001.6(b) applicants bring the following co-pending application to the Examiner's attention: Applicant: Duncaif, et al., U.S. Appl. No. 12/309,295, filed Jan. 13, 2009, For: Relating to Anti-Parasitic Compositions.

Pursuant to MPEP § 2001.6(b) applicants bring the following co-pending application to the Examiner's attention: Applicant: Duncalf, et al., U.S. Appl. No. 12/309,293, filed Jan. 13, 2009, For: Biocidal Compositions.

Pursuant to MPEP § 2001.6(b) applicants bring the following co-pending application to the Examiner's attention: Applicant: Duncalf, et al., U.S. Appl. No. 12/309,294, filed Jan. 13, 2009, For: Relating to Pharmaceutical Compositions.

Pursuant to MPEP § 2001.6(b) applicants bring the following co-pending application to the Examiner's attention: Applicant: Duncalf, et al., U.S. Appl. No. 12/309,292, filed Jan. 13, 2009, For: Relating to Pharmaceutical Compositions.

GB 0613925.7 Great Britain Search Report dated Nov. 13, 2006 (1 page).

* cited by examiner

PREPARATION OF PHARMACEUTICAL COMPOSITIONS

This application is a US national Stage of PCT/GB2007/050407, filed Jul. 13, 2007, and claims priority to and benefit of GB application 0613925.7, filed Jul. 13, 2006, and PCT/EP2007/056560, filed Jun. 29, 2007.

FIELD OF THE INVENTION

The present invention relates to improvements relating to pharmaceutical compositions. In particular it relates to pharmaceutically active compositions and precursors therefor which fall within the group of analgesics including paracetamol and non-steroidal anti-inflammatory agents.

BACKGROUND OF THE INVENTION

Non-steroidal anti-inflammatory drugs, usually abbreviated to NSAIDs, are drugs with analgesic, antipyretic and anti-inflammatory effects. As analgesics, NSAIDs are unusual in that they are non-narcotic. NSAIDs are sometimes also referred to as non-steroidal anti-inflammatory agents/analgesics (NSAIAs) or non-steroidal anti-inflammatory medicines (NSAIMs). The most prominent members of this group of drugs are aspirin and ibuprofen. Paracetamol (acetaminophen) has negligible anti-inflammatory activity, and is strictly speaking not an NSAID.

The exact mechanism of action of paracetamol is uncertain, but it appears to be acting on the central nervous system. Aspirin and the other NSAIDs inhibit cyclooxygenase, leading to a decrease in prostaglandin production; this reduces pain and also inflammation (in contrast to paracetamol and opioids).

NSAIDs can be broadly classified based on their chemical structure. NSAIDs within a group will tend to have similar characteristics and tolerability. There is little difference in clinical efficacy between the NSAIDs when used at equivalent doses. Rather, differences between compounds tended to be with regards to dosing regimens (related to the compound's elimination half-life), route of administration, and tolerability profile.

Salicylates include: Aspirin, Amoxiprin, Benorilate, Choline magnesium salicylate, Diflunisal, Faislamine, Methyl salicylate, Magnesium Salicylate and Salicyl salicylate (salsalate). Arylalkanoic acids include: Diclofenac, Aceclofenac, Acemetacin, Bromfenac, Etodolac, Indometacin, Nabumetone, Sulindac and Tolmetin. 2-Arylpropionic acids (profens) include: Ibuprofen, Carprofen, Fenbufen, Fenoprofen, Flurbiprofen, Ketoprofen, Ketorolac, Loxoprofen, Naproxen, Tiaprofenic acid and Suprofen. N-Arylanthranilic acids (fenamic acids) include: Mefenamic acid and Meclofenamic acid. Pyrazolidine derivatives include: Phenylbutazone, Azapropazone, Metamizole, Oxyphenbutazone and Sulfinprazone. Oxicams include: Piroxicam, Lornoxicam, Meloxicam and Tenoxicam. COX-2 Inhibitors include: Celecoxib, Etoricoxib, Lumiracoxib, Parecoxib, Rofecoxib and Valdecoxib. Sulphonanilides include Nimesulide and other NSAIDs include Licofelone and Omega-3 Fatty Acids.

Paracetamol and many NSAIDs exhibit low water solubility and are practically insoluble in water. This hinders some aspects of their use for oral administration, including rapidity of action onset.

WO 2004/011537 describes the formation of solid, porous beads comprising a three dimensional open-cell lattice of a water-soluble polymeric material. These are typically "templated" materials formed by the removal of both water and a non-aqueous dispersed phase from a high internal phase emulsion (HIPE) which has a polymer dissolved in the aqueous phase. The beads are formed by dropping the HIPE emulsion into a low temperature fluid such as liquid nitrogen, then freeze-drying the particles formed to remove the bulk of the aqueous phase and the dispersed phase. This leaves behind the polymer in the form of a "skeletal" structure. The beads dissolve rapidly in water and have the remarkable property that a water-insoluble component dispersed in the dispersed phase of the emulsion prior to freezing and drying can also be dispersed in water on solution of the polymer skeleton of the beads.

WO 2005/011636 discloses a non-emulsion based spray drying process for forming "solid amorphous dispersions" of drugs in polymers. In this method a polymer and a low-solubility drug are dissolved in a solvent and spray-dried to form dispersions in which the drug is mostly present in an amorphous form rather than in a crystalline form.

Unpublished co-pending applications (GB 0501835 of 28 Jan. 2005 and GB 0613925 filed on 13 Jul. 2006) describe how materials which will form a nano-dispersion in water can be prepared, preferably by a spray-drying process. In the first of these applications the water insoluble materials is dissolved in the solvent-phase of an emulsion. In the second, the water-insoluble materials are dissolved in a mixed solvent system and co-exist in the same phase as a water-soluble structuring agent. In both cases the liquid is dried above ambient temperature (above 20° C.), such as by spray drying, to produce particles of the structuring agent, as a carrier, with the water-insoluble materials dispersed therein. When these particles are placed in water they dissolve, forming a nano-dispersion of the water-insoluble material with particles typically below 300 nm. This scale is similar to that of virus particles, and the water-insoluble material behaves as though it were in solution.

WO 2007/53197 (Elan Pharma International Ltd) discloses nanoparticulate forms of acetaminophen. Particle sizes of less than 2000 nm are disclosed. The nanoparticulate acetaminophen, or a salt or derivative thereof, compositions can be made using, for example, milling, homogenization, precipitation, freezing, or template emulsion techniques.

In the present application the term "ambient temperature" means 20° C. and all percentages are percentages by weight unless otherwise specified.

BRIEF DESCRIPTION OF THE INVENTION

We have now determined that both the emulsion-based and the single-phase method can be used to produce a water-soluble, nano-disperse form of paracetamol or an NSAID.

Accordingly, the present invention provides a process for the production of a composition comprising a water-insoluble paracetamol or NSAID which comprises the steps of:
a) providing a mixture comprising:
   i) a water-insoluble paracetamol or NSAID,
   ii) a water soluble carrier, and
   iii) a solvent for each of the paracetamol or NSAID and the carrier; and
b) spray-drying the mixture to remove the or each solvent and obtain a substantially solvent-free nano-dispersion of the paracetamol or NSAID in the carrier.

The preferred method of particle sizing for the dispersed products of the present invention employs a dynamic light scattering instrument (Nano S, manufactured by Malvern Instruments, UK). Specifically, the Malvern Instruments Nano S uses a red (633 nm) 4 mW Helium-Neon laser to illuminate a standard optical quality UV cuvette containing a suspension of material. The particle sizes quoted in this application are those obtained with that apparatus using the standard protocol. Particle sizes in solid products are the particle sizes inferred from the measurement of the particle size obtained by solution of the solid in water and measurement of the particle size.

Preferably, the peak diameter of the water-insoluble active agent is below 1500 nm. More preferably the peak diameter of the water-insoluble active agent is below 1000 nm, most preferably below 800 nm. In a particularly preferred embodiment of the invention the median diameter of the water-insoluble active agent is in the range 200 to 800 nm, more preferably 400 to 600 nm.

Advantageous compositions obtainable by the process of the present invention comprise a water-insoluble active agent (paracetamol or an NSAID) and a water soluble carrier which comprises active agent particles of approximately 500 nm average particle size dispersed in the carrier.

It is believed that reduction of the particle size in the eventual nano-dispersion has significant advantages in improving the availability of the otherwise water-insoluble material. This is believed to be particularly advantageous where an improved bio-availability is sought, or, in similar applications where high local concentrations of the material are to be avoided. Moreover it is believed that nano-dispersions with a small particle size are more stable than those with a larger particle size.

In the context of the present invention, "water insoluble" as applied to the paracetamol or NSAID means that its solubility in water is less than 25 g/L. "Water insoluble paracetamol or NSAID" may also mean that the solubility is less than 20 or less than 15 g/L. Preferably, the water insoluble paracetamol or NSAID has solubility in water at ambient temperature (20° C.) less than 5 g/L preferably of less than 1 g/L, especially preferably less than 150 mg/L, even more preferably less than 100 mg/L. This solubility level provides the intended interpretation of what is meant by water-insoluble in the present specification.

Paracetamol is very slightly soluble in cold water (Merck Index monograph). Preferred water-insoluble NSAIDs include insoluble salts, acids and bases of ketoprofen, naproxen, diclofenac and ketoralac and water insoluble derivatives thereof.

Preferred carrier materials are selected from the group consisting of water-soluble organic and inorganic materials, surfactants, polymers and mixtures thereof.

A further aspect of the present invention provides a process for preparing a paracetamol or NSAID composition comprising a water-insoluble paracetamol or NSAID and a water-soluble carrier, which comprises the steps of:
 a) forming an emulsion comprising:
  i) a solution of the paracetamol or NSAID in a water-immiscible solvent for the same, and
  ii) an aqueous solution of the carrier; and
 b) drying the emulsion to remove water and the water-immiscible solvent to obtain a substantially solvent-free nano-dispersion of the paracetamol or NSAID in the carrier.

For convenience, this class of method is referred to herein as the "emulsion" method.

A further aspect of the present invention provides a process for preparing a paracetamol or NSAID composition comprising a water insoluble paracetamol or NSAID and a water-soluble carrier which comprises the steps of:
 a) providing a single phase mixture comprising:
  i) at least one non-aqueous solvent,
  ii) optionally, water,
  iii) a water-soluble carrier material soluble in the mixture of (i) and (ii), and
  iv) a water-insoluble paracetamol or NSAID which is soluble in the mixture of (i) and (ii); and
 b) drying the solution to remove water and the water miscible solvent to obtain a substantially solvent-free nano-dispersion of the paracetamol or NSAID in the carrier.

For convenience, this class of method is referred to herein as the "single-phase" method.

In the context of the present invention substantially solvent free means within limits accepted by international pharmaceutical regulatory bodies (eg FDA, EMEA) for residual solvent levels in a pharmaceutical product and/or that the free solvent content of the product is less than 15% wt, preferably below 10% wt, more preferably below 5% wt and most preferably below 2% wt.

In the context of the present invention it is essential that both the carrier material and the paracetamol or NSAID are essentially fully dissolved in their respective solvents prior to the drying step. It is not within the ambit of the present specification to teach the drying of slurries. For the avoidance of any doubt, it is therefore the case that the solids content of the emulsion or the mixture is such that over 90% wt, preferably over 95%, and more preferably over 98% of the soluble materials present is in solution prior to the drying step.

In relation to the methods mentioned above, the preferred active agents and the preferred carrier materials are as described above and as elaborated on in further detail below. Similarly the preferred physical characteristics of the material are as described above.

The "single phase" method where both the paracetamol or NSAID and the carrier material are dissolved in a phase comprising at least one other non-aqueous solvent (and optional water) is preferred. This is believed to be more efficacious in obtaining a smaller particle size for the nano-disperse paracetamol or NSAID. Preferably, the drying step simultaneously removes both the water and other solvents and, more preferably, drying is accomplished by spray drying at above ambient temperature.

The products obtainable by the process aspects of the present invention are suitable for use in the preparation of medicaments for treatment of pain.

DETAILED DESCRIPTION OF THE INVENTION

Various preferred features and embodiments of the present invention are described in further detail below.

Paracetamol and NSAIDs

As noted above the preferred water-insoluble paracetamol and NSAIDs include insoluble salts, acids and bases of ketoprofen, naproxen, diclofenac and ketoralac and water insoluble derivatives and mixtures thereof. In one embodiment of the present invention, the NSAID is not aspirin or ibuprofen.

The water-insoluble paracetamol and NSAIDs can be present as the sole pharmaceutically active ingredient in compositions according to the present invention or be together with other drugs to provide a so-called "combination therapy".

As an illustrative example, it would be beneficial to provide a combination of paracetamol or an NSAID such as diclofenac, ibuprofen or naproxen with a further therapeutically active agent, such as a triptan such as sumatriptan, to treat migraine and headaches, such as cluster headaches. In one embodiment, the invention does not include the combination of an NSAID or paracetamol and a triptan such as sumatriptan. As a second illustrative example, it would be beneficial to provide a treatment of GERD (GastroEsophageal Reflux Disease) comprising a combination of paracetamol or an NSAID such as diclofenac, ibuprofen or naproxen with a further therapeutically active agent known to be useful in treating GERD, such as a proton pump inhibitor (for example omeprazole or esomeprazole) or an $H_2$ antagonist (for example ranitidine or famotidine).

Water-Dispersible Product Form

The present invention provides a method for obtaining a water-dispersible form of an otherwise water-insoluble material. This is prepared by forming a not wholly aqueous intermediate emulsion or solution in which both a water-soluble carrier material and the water insoluble paracetamol or NSAID are dissolved. On removal of solvents the insoluble paracetamol or NSAID is left dispersed through the water-soluble carrier material. Suitable carrier materials are described in further detail below.

The structure of the material obtained after the drying step is not well understood. It is believed that the resulting dry materials are not encapsulates, as discrete macroscopic bodies of the water-insoluble materials are not present in the dry product. Neither are the dry materials "dry emulsions" as little or none of the volatile solvent comprising the "oil" phase of the emulsion remains after the drying step. On addition of water to the dry product the emulsion is not reformed, as it would be with a "dry emulsion". It is also believed that the compositions are not so-called solid solutions, as with the present invention the ratios of components present can be varied without loss of the benefits. Also from X-ray and DSC studies, it is believed that the compositions of the invention are not solid solutions, but comprise nano-scale, phase-separated mixtures. Further, from X-ray powder diffraction studies it is believed that the paracetamol or NSAID nano-particle material produced is in crystalline form and not amorphous form and it is believed to be predominantly or entirely the same crystalline form as the starting material.

Preferably, the compositions produced after the drying step will comprise the active agent and the carrier in a weight ratio of from 1:500 to 1:1 (as active:carrier), 1:100 to 1:1 being preferred. Typical levels of around 10-50% wt water-insoluble paracetamol or NSAID and 90-50% wt carrier can be obtained by spray drying.

By the method of the present invention the particle size of the active agent materials can be reduced to below 1000 nm and may be reduced to around 100 nm. Preferred particle sizes are in the range 400-800 nm.

"Emulsion" Preparation Method

In one preferred method according to the invention the solvent for the water-insoluble paracetamol or NSAID is not miscible with water. On admixture with water it therefore can form an emulsion.

Preferably, the non-aqueous phase comprises from about 10% to about 95% v/v of the emulsion, more preferably from about 20% to about 68% v/v.

The emulsions are typically prepared under conditions which are well known to those skilled in the art, for example, by using a magnetic stirring bar, a homogeniser, or a rotational mechanical stirrer. The emulsions need not be particularly stable, provided that they do not undergo extensive phase separation prior to drying.

Homogenisation using a high-shear mixing device is a particularly preferred way to make an emulsion in which the aqueous phase is the continuous phase. It is believed that this avoidance of coarse emulsion and reduction of the droplet size of the dispersed phase of the emulsion, results in an improved dispersion of the "payload" material in the dry product.

In a preferred method according to the invention a water-continuous emulsion is prepared with an average dispersed-phase droplet size (using the Malvern peak intensity) of between 500 nm and 5000 nm. We have found that an Ultra-Turrux T25 type laboratory homogenizer (or equivalent) gives a suitable emulsion when operated for more than a minute at above 10,000 rpm.

There is a directional relation between the emulsion droplet size and the size of the particles of the payload material, which can be detected after dispersion of the materials of the invention in aqueous solution. We have determined that an increase in the speed of homogenization for precursor emulsions can decrease final particle size after re-dissolution.

It is believed that the re-dissolved particle size can be reduced by nearly one half when the homogenization speed increased from 13,500 rpm to 21,500 rpm. The homogenization time is also believed to play a role in controlling re-dissolved particle size. The particle size again decreases with increase in the homogenization time, and the particle size distribution become broader at the same time.

Sonication is also a particularly preferred way of reducing the droplet size for emulsion systems. We have found that a Hert Systems Sonicator XL operated at level 10 for two minutes is suitable.

It is believed that ratios of components which decrease the relative concentration of the active agent to the solvents and/or the carrier give a smaller particle size.

"Single Phase" Preparation Method

In an alternative method according to the present invention both the carrier and the paracetamol or NSAID are soluble in a non-aqueous solvent or a mixture of such a solvent with water. Both here and elsewhere in the specification the non-aqueous solvent can be a mixture of non-aqueous solvents.

In this case the feedstock of the drying step can be a single phase material in which both the water-soluble carrier and the water-insoluble paracetamol or NSAID are dissolved. It is also possible for this feedstock to be an emulsion, provided that both the carrier and the active agent are dissolved in the same phase.

The "single-phase" method is generally believed to give a better nano-dispersion with a smaller particle size than the emulsion method.

It is believed that ratios of components which decrease the relative concentration of the active agent to the solvents and/or the carrier give a smaller particle size.

Drying

Spray drying is well known to those versed in the art. In the case of the present invention some care must be taken due to the presence of a volatile non-aqueous solvent in the emulsion being dried. In order to reduce the risk of explosion when a flammable solvent is being used, an inert gas, for example nitrogen, can be employed as the drying medium in a so-called closed spray-drying system. The solvent can be recovered and re-used.

We have found that the Buchi B-290 type laboratory spray drying apparatus is suitable.

It is preferable that the drying temperature should be at or above 100° C., preferably above 120° C. and most preferably above 140° C. Elevated drying temperatures have been found to give smaller particles in the re-dissolved nano-disperse material.

Carrier Material

The carrier material is water soluble, which includes the formation of structured aqueous phases as well as true ionic solution of molecularly mono-disperse species. The carrier material preferably comprises an inorganic material, surfactant, a polymer or may be a mixture of two or more of these.

It is envisaged that other non-polymeric, organic, water-soluble materials such as sugars can be used as the carrier. However the carrier materials specifically mentioned herein are preferred.

Suitable carrier materials (referred to herein as "water soluble carrier materials") include preferred water-soluble polymers, preferred water-soluble surfactants and preferred water-soluble inorganic materials.

Preferred Polymeric Carrier Materials

Examples of suitable water-soluble polymeric carrier materials include
- (a) natural polymers (for example naturally occurring gums such as guar gum, alginate, locust bean gum or a polysaccharide such as dextran;
- (b) cellulose derivatives for example xanthan gum, xyloglucan, cellulose acetate, methylcellulose, methyl-ethylcellulose, hydroxy-ethylcellulose, hydroxy-ethylmethyl-cellulose, hydroxy-propylcellulose, hydroxy-propylmethylcellulose, hydroxy-propylbutylcellulose, ethylhydroxy-ethylcellulose, carboxy-methylcellulose and its salts (e.g. the sodium salt—SCMC), or carboxymethylhydroxyethylcellulose and its salts (for example the sodium salt);
- (c) homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethylacrylate, vinyl pyrrolidone, vinyl imidazole, vinyl amines, vinyl pyridine, ethyleneglycol and other alkylene glycols, ethylene oxide and other alkylene oxides, ethyleneimine, styrenesulphonates, ethyleneglycolacrylates and ethyleneglycol methacrylate;
- (d) cyclodextrins, for example β-cyclodextrin; and
- (e) mixtures thereof.

When the polymeric material is a copolymer it may be a statistical copolymer (heretofore also known as a random copolymer), a block copolymer, a graft copolymer or a hyperbranched copolymer. Co-monomers other than those listed above may also be included in addition to those listed if their presence does not destroy the water soluble or water dispersible nature of the resulting polymeric material.

Examples of suitable and preferred homopolymers include poly-vinylalcohol, poly-acrylic acid, poly-methacrylic acid, poly-acrylamides (such as poly-N-isopropylacrylamide), poly-methacrylamide; poly-acrylamines, poly-methylacrylamines, (such as polydimethylaminoethylmethacrylate and poly-N-morpholinoethylmethacrylate), polyvinylpyrrolidone, poly-styrenesulphonate, polyvinylimidazole, polyvinylpyridine, poly-2-ethyl-oxazoline poly-ethyleneimine and ethoxylated derivatives thereof.

Polyethylene glycol (PEG), polyvinylpyrrolidone (PVP), poly(2-ethyl-2-oxazaline), polyvinyl alcohol (PVA) hydroxypropyl cellulose and hydroxypropyl-methyl cellulose (HPMC) and alginates are preferred polymeric carrier materials.

Preferred Surfactant Carrier Materials

Where the carrier material is a surfactant, the surfactant may be non-ionic, anionic, cationic, amphoteric or zwitterionic.

Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; and alkyl polyglycosides.

Examples of suitable anionic surfactants include alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; and isethionate sulfonates.

Examples of suitable cationic surfactants include fatty amine salts; fatty diamine salts; quaternary ammonium compounds; phosphonium surfactants; sulfonium surfactants; and sulfonxonium surfactants.

Examples of suitable zwitterionic surfactants include N-alkyl derivatives of amino acids (such as glycine, betaine, aminopropionic acid); imidazoline surfactants; amine oxides; and amidobetaines.

Mixtures of surfactants may be used. In such mixtures there may be individual components which are liquid, provided that the carrier material overall, is a solid.

Alkoxylated nonionics (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB) are particularly preferred as surfactant carrier materials.

Preferred Inorganic Carrier Materials

The carrier material can also be a water-soluble inorganic material which is neither a surfactant nor a polymer. Simple organic salts have been found suitable, particularly in admixture with polymeric and/or surfactant carrier materials as described above. Suitable salts include carbonate, bicarbonates, halides, sulphates, nitrates and acetates, particularly soluble salts of sodium, potassium and magnesium. Preferred materials include sodium carbonate, sodium bicarbonate and sodium sulphate. These materials have the advantage that they are cheap and physiologically acceptable. They are also relatively inert as well as compatible with many materials found in pharmaceutical products.

Mixtures of carrier materials are advantageous. Preferred mixtures include combinations of surfactants and polymers, which include at least one of:
- a) polyethylene glycol (PEG), polyvinylpyrrolidone (PVP), hydroxypropyl cellulose and hydroxypropylmethyl cellulose (HPMC), and alginates;

and at least one of:
- b) alkoxylated nonionics (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB).

The carrier material can also be a water-soluble small organic material which is neither a surfactant, a polymer nor an inorganic carrier material. Simple organic sugars have been found to be suitable, particularly in admixture with a polymeric and/or surfactant carrier material as described above. Suitable small organic materials include mannitol, polydextrose, xylitol, maltitol, dextrose, dextrins, dextrans, maltodextrin and inulin, etc.

Non-Aqueous Solvent

The compositions of the invention comprise a volatile, second non-aqueous solvent. This may either be miscible with the other solvents in pre-mix before drying or, together with those solvents may form an emulsion.

In one alternative form of the invention a single, non-aqueous solvent is employed in which can form a single phase with water in the presence of the paracetamol or NSAID and the carrier. Preferred solvents for these embodiments are polar, protic or aprotic solvents. Generally preferred solvents have a dipole moment greater than 1 and a dielectric constant greater than 4.5.

Particularly preferred solvents are selected from the group consisting of haloforms (preferably dichloromethane, chloroform), lower (C1-C10) alcohols (preferably methanol, ethanol, isopropanol, isobutanol), organic acids (preferably formic acid, acetic acid), amides (preferably formamide, N,N-dimethylformamide), nitriles (preferably aceto-nitrile), esters (preferably ethyl acetate) aldehydes and ketones (preferably methyl ethyl ketone, acetone), and other water miscible species comprising heteroatom bond with a suitably large dipole (preferably tetrahydrofuran, dialkylsulphoxide).

Haloforms, lower alcohols, ketones and dialkylsulphoxides are the most preferred solvents.

In another alternative form of the invention the non-aqueous solvent is not miscible with water and forms an emulsion.

The non-aqueous phase of the emulsion is preferably selected from one or more from the following group of volatile organic solvents:
  alkanes, preferably heptane, n-hexane, isooctane, dodecane, decane;
  cyclic hydrocarbons, preferably toluene, xylene, cyclohexane;
  halogenated alkanes, preferably dichloromethane, dichoroethane, trichloromethane (chloroform), fluorotrichloromethane and tetrachloroethane;
  esters, preferably ethyl acetate;
  ketones, preferably 2-butanone;
  ethers, preferably diethyl ether;
  volatile cyclic silicones, preferably either linear or cyclomethicones containing from 4 to 6 silicon units. Suitable examples include DC245 and DC345, both of which are available from Dow Corning Inc.

Preferred solvents include dichloromethane, chloroform, ethanol, acetone and dimethyl sulphoxide.

Preferred non-aqueous solvents, whether miscible or not, have a boiling point of less than 150° C. and, more preferably, have a boiling point of less than 100° C., so as to facilitate drying, particularly spray-drying under practical conditions and without use of specialised equipment. Preferably they are non-flammable, or have a flash point above the temperatures encountered in the method of the invention.

Preferably, the non-aqueous solvent comprises from about 10% to about 95% v/v of any emulsion formed, more preferably from about 20% to about 80% v/v. In the single phase method the level of solvent is preferably 20-100% v/v.

Particularly preferred solvents are alcohols, particularly ethanol and halogenated solvents, more preferably chlorine-containing solvents, most preferably solvents selected from (di- or trichloromethane).

Optional Cosurfactant

In addition to the non-aqueous solvent an optional co-surfactant may be employed in the composition prior to the drying step. We have determined that the addition of a relatively small quantity of a volatile cosurfactant reduced the particle diameter of the material produced. This can have a significant impact on particle volume. For example, reduction from 297 nm to 252 nm corresponds to a particle size reduction of approximately 40%. Thus, the addition of a small quantity of co-surfactant offers a simple and inexpensive method for reducing the particle size of materials according to the present invention without changing the final product formulation.

Preferred co-surfactants are short chain alcohols or amine with a boiling point of <220° C.

Preferred co-surfactants are linear alcohols. Preferred co-surfactants are primary alcohols and amines. Particularly preferred co-surfactants are selected from the group consisting of the 3-6 carbon alcohols. Suitable alcohol co-surfactants include n-propanol, n-butanol, n-pentanol, n-hexanol, hexylamine and mixtures thereof.

Preferably the co-surfactant is present in a quantity (by volume) less than the solvent preferably the volume ratio between the solvent and the co-surfactant falls in the range 100:40 to 100:2, more preferably 100:30 to 100:5.

Preferred Spray-Drying Feedstocks

Typical spray drying feedstocks comprise:
  a) a surfactant;
  b) at least one lower alcohol;
  c) more than 0.1% of at least one water-insoluble paracetamol or NSAID dissolved in the feedstock;
  d) a polymer; and,
  e) optional water.

Preferred spray-drying feedstocks comprise:
  a) at least one non-aqueous solvent selected from dichloromethane, chloroform, ethanol, acetone, and mixtures thereof;
  b) a surfactant selected from PEG co-polymer nonionics (especially the PEG/PPG Pluronic™ materials), alkyl sulphonates (especially SDS), ester surfactants (preferably sorbitan esters of the Span™ and Tween™ types) and cationics (especially cetyltrimethylammonium bromide—CTAB) and mixtures thereof;
  c) more than 0.1% of at least one water-insoluble paracetamol or NSAID;
  d) a polymer selected from Polyethylene glycol (PEG), Polyvinyl alcohol (PVA), polyvinyl-pyrrolidone (PVP), hydroxypropyl cellulose and hydroxypropyl-methyl cellulose (HPMC), alginates and mixtures thereof; and
  e) optionally, water.

The drying feed-stocks used in the present invention are either emulsions or solutions which preferably do not contain any solid matter and in particular preferably do not contain any undissolved active agent.

The level of the paracetamol or NSAID in the composition may be up to 95% wt, up to 90%, up to 85%, up to 80%, up to 75%, up to 70%, up to 65%, up to 60%, up to 55%, up to 50%, up to 45%, up to 40%, up to 35% or up to 30%. In some embodiments, it is particularly preferable that the level of the active agent in the composition should be such that the loading in the dried composition is below 40% wt, and more preferably below 30% wt. Such compositions have the advantages of a small particle size and high effectiveness as discussed above.

Water-Dispersed Form

On admixture of the water-soluble carrier material with water, the carrier dissolves and the water-insoluble paracetamol or NSAID is dispersed through the water in sufficiently fine form that it behaves like a soluble material in many respects. The particle size of the water-insoluble materials in the dry product is preferably such that, on solution in water the water-insoluble materials have a particle size of less than 1 μm as determined by the Malvern method described herein. It is believed that there is no significant reduction of particle size for the active agent on dispersion of the solid form in water.

By applying the present invention significant levels of "water-insoluble" materials can be brought into a state which is largely equivalent to true solution. When the dry product is dissolved in water it is possible to achieve optically clear solutions comprising more than 0.1%, preferably more than 0.5% and more preferably more than 1% of the water-insoluble material.

It is envisaged that the solution form will be a form suitable for administration to a patient either "as is" or following further dilution. In the alternative, the solution form of embodiments of the invention may be combined with other active materials to yield a medicament suitable for use in combination therapy.

EXAMPLES

In order that the present invention may be further understood and carried forth into practice it is further described below with reference to non-limiting examples.

A range of formulations were produced based on different excipients, different active loadings, and different process conditions. The formulations include paracetamol as an illustrative example of an active agent according to the present invention, but could equally have been prepared using one of the other available water insoluble NSAIDs.

The excipients were chosen from hydroxypropyl cellulose (Klucel EF, Herlus), polyvinyl pyrrolidone (PVP k30, Aldrich), hydroxypropyl methyl cellulose (HPMC, Mw 10 k, 5 cps, Aldrich), polyethylene glycol (PEG, Mw 6,000, Fluka), Tween 80 (Aldrich), pluronic F68 (BASF), pluronic F127 (Aldrich), span 80 (Aldrich), cremphor RH40 (BASF), mannitol (Aldrich), and sodium alginate (Aldrich).

Details of these formulations are listed as below:

Example 1

20 wt % Loadings 0.40 g Paracetamol, 1.00 g Klucel EF, 0.44 g HPMC, and 0.16 g Pluronic F68 are all dispersed into 100 ml absolute ethanol. The ethanol suspension is stirred intensively with a magnetic bar for about half hour before adding 60 ml distilled water. A clear solution is obtained.

The solution is then spray dried with a BUCHI Mini B-290 spray dryer at 120° C. with the liquid feed rate at 2.5 ml/min. A white free flowing powder is obtained.

20 mg dried powder is dispersed into 10 nil distilled water, giving a crystal clear nanodispersion with a particle size of between 100 and 500 nm.

Example 2

20 wt % Loadings 0.40 g Paracetamol, 1.00 g Klucel EF, 0.34 g HPMC, 0.16 g Pluronic F127, and 0.10 g Tween 80 are all dispersed into 100 ml absolute ethanol. The ethanol suspension is stirred intensively with a magnetic bar for about half hour before adding 60 ml distilled water. A clear solution is obtained.

The solution was then spray dried with a BUCHI Mini B-290 spray dryer at 120° C. with the liquid feed rate at 2.5 ml/min. A white free flowing powder is obtained.

20 mg dried powder is dispersed into 10 ml distilled water, giving a crystal clear nanodispersion with a particle size of 100 to 500 nm.

Two dissolution tests based on a 20 mg paracetamol dose and an 80 mg paracetamol dose are carried out using the standard USP2 test. 50% of the 20 mg dose is expected to dissolve within less than 10 minutes and 50% of the 80 mg dose within 30 minutes. 95% of the 20 mg dose is expected to dissolve within less than 60 minutes and 95% of the 80 mg dose within less than 150 minutes.

Example 3

20 wt % Loadings 0.40 g Paracetamol, 1.00 g Klucel EF, and 0.60 g HPMC are all dispersed into 100 ml absolute ethanol. The ethanol suspension is stirred intensively with a magnetic bar for about half hour before adding 60 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder was dispersed into 10 ml distilled water, giving a crystal clear nanodispersion with a particle size of between 100 and 500 nm.

Example 4

20 wt % Loadings 0.40 g Paracetamol, 1.44 g Klucel EF, and 0.16 g PEG 6000 are all dispersed into 100 ml absolute ethanol. The ethanol suspension is stirred intensively with a magnetic bar for about half hour and a clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a translucent nanodispersion with a particle size of between 300 and 800 nm.

Example 5

20 wt % Loadings 0.40 g Paracetamol, 1.00 g Klucel EF, 0.18 g HPMC, 0.16 g PEG 6000, 0.16 g Pluronic F127, and 0.10 g Tween 80 are all dispersed into 100 ml absolute ethanol. The ethanol suspension is stirred intensively with magnetic bar for about half hour before adding 60 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of 100 to 200 nm.

Example 6

20 wt % Loadings 0.40 g Paracetamol, 1.34 g Klucel EF, 0.16 g Pluronic F127, and 0.10 g Cremphor RH40 are all dispersed into 100 ml absolute ethanol. The ethanol suspension is stirred intensively with a magnetic bar for about half hour before adding 60 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder was dispersed into 10 ml distilled water, giving a crystal clear nanodispersion with a particle size of between 100 and 200 nm.

Two dissolution tests based on a 20 mg paracetamol dose and an 80 mg paracetamol dose are carried out for formulations following the standard USP2 test. 50% of the mg dose is expected to dissolve within less than 10 minutes and 50% of the 80 mg dose within less than 5 minutes. 95% of the 20 mg dose is expected to dissolve within less than 25 minutes and 95% of the 80 mg dose within less than 90 minutes.

Example 7

20 wt % Loadings 0.40 g Paracetamol, 1.18 g Klucel EF, 0.16 g Pluronic F68, 0.16 g Pluronic F127, and 0.10 g Span 80 are all dispersed into 100 ml absolute ethanol. The ethanol suspension is stirred intensively with a magnetic bar for about half hour before adding 10 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 100 and 300 nm.

Example 8

20 wt % Loadings 0.40 g Paracetamol, 1.40 g Klucel EF, 0.10 g Tween 80, and 0.10 g Span 80 are all dispersed into 100 ml absolute ethanol. The ethanol suspension is stirred intensively with a magnetic bar for about half hour and a clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 100 and 300 nm.

Example 9

30 wt % Loadings 0.30 g Paracetamol, 0.57 g Klucel EF, 0.05 g PEG 6000, 0.05 g Pluronic F127, and 0.03 g Tween 80 are all dispersed into 50 ml absolute ethanol. The ethanol suspension is stirred intensively with a magnetic bar for about half hour before adding 30 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 100 and 400 nm.

Example 10

30 wt % Loadings 0.30 g Paracetamol, 0.65 g Klucel EF, 0.025 g Tween 80, and 0.025 g Span 80 are all dispersed into 50 ml absolute ethanol. The ethanol suspension is stirred intensively with a magnetic bar for about half hour and a clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a translucent nanodispersion with a particle size of between 200 and 400 nm.

Example 11

20 wt % Loadings 0.20 g Paracetamol, 0.40 g Klucel EF, 0.10 g Pluronic F127, 0.10 g Tween 80, and 0.20 g Mannitol are all dispersed into 50 ml absolute ethanol. The ethanol suspension is stirred intensively with a magnetic bar for about half hour before added 30 ml distilled water. A clear solution is obtained.

The solution is then spray dried with a BUCHI Mini B-290 spray dryer at 140° C. with the liquid feed rate at 2.5 ml/min. A white free flowing powder is obtained.

20 mg dried powder is dispersed into 10 ml distilled water, giving a crystal clear nanodispersion with a particle size of between 100 and 300 nm.

A dissolution test based on a 20 mg paracetamol dose is carried out for formulation obtained from Example 11 following the standard USP2 test. 50% of the 20 mg dose is expected to dissolve within less than 5 minutes and 95% within less than 10 minutes.

Example 12

20 wt % Loadings 0.20 g Paracetamol, 0.50 g Klucel EF, 0.10 g Pluronic F127, and 0.20 g Mannitol are all dispersed into 50 ml absolute ethanol. The ethanol suspension is stirred intensively with a magnetic bar for about half hour before adding 30 ml distilled water. A clear solution is obtained.

The solution is then spray dried with a BUCHI Mini B-290 spray dryer at 140° C. with the liquid feed rate at 2.5 ml/min. A white free flowing powder is obtained.

20 mg dried powder is dispersed into 10 ml distilled water, giving a crystal clear nanodispersion with a particle size of between 100 and 300 nm.

A dissolution test based on a 20 mg paracetamol dose is carried out for following the standard USP2 test. 95% of the 20 mg dose is expected to dissolve within less than 5 minutes.

Example 13

20 wt % Loadings 0.20 g Paracetamol, 0.60 g Klucel EF, 0.05 g Pluronic F127, 0.05 g Tween 80, and 0.10 g Mannitol are all dispersed into 50 ml absolute ethanol. The ethanol suspension is stirred intensively with a magnetic bar for about half hour before adding 30 ml distilled water. A clear solution is obtained.

The solution is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 100 and 300 nm.

Example 14

20 wt % Loadings 0.20 g Paracetamol, 0.60 g Klucel EF, 0.10 g Pluronic F127, 0.025 g Tween 80, and 0.025 g Span 80 are all dispersed into 50 ml absolute ethanol. The ethanol suspension is stirred intensively with a magnetic bar for about half hour and a clear ethanol solution was formed. 0.05 g Sodium alginate is dissolved into 30 ml distilled water. The ethanol solution and the aqueous solution are mixed together and a clear mixture is obtained.

The mixture is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 100 and 400 nm.

Example 15

20 wt % Loadings 0.20 g Paracetamol, 0.60 g Klucel EF, 0.15 g Pluronic F127 are all dispersed into 50 ml absolute ethanol. The ethanol suspension is stirred intensively with a magnetic bar for about half hour. 0.05 g Sodium alginate is dissolved into 30 ml distilled water. The ethanol dispersion and the aqueous solution are mixed together and a clear mixture is obtained.

The mixture is then spray dried with a BUCHI Mini B-290 spray dryer at 160° C. with the liquid feed rate at 2.5 ml/min. A white free flowing powder is obtained.

20 mg dried powder is dispersed into 10 ml distilled water, giving a crystal clear nanodispersion with a particle size of between 200 and 400 nm.

A dissolution test based on a 20 mg paracetamol dose is carried out for the formulation prepared in Example 15 following the standard USP2 test. 50% of the mg dose is expected to dissolve within less than 5 minutes and 95% within less than 90 minutes.

Example 16

This example summarises the experimental conditions used to produce a spray dried paracetamol formulation.

The following materials were used as purchased, without further purification:
4-Acetamidophenol (Paracetamol, 98%, Mw 151.17, Aldrich)
Hydroxypropyl methyl cellulose (HPMC, Mw 10,000, Aldrich)
Sodium dodecylsulphate (SDS, 98% Mw 288. 18, BDH)
Tween 80 (Mw 1309, Aldrich),
Plutonic F-127 (Sigma)
Mannitol (Mw 182.17, Aldrich)

Paracetamol and the excipients were dissolved into 200 ml water/ethanol co-solvent (50% v/v) and the resulting solution was then spray dried on a Buchi B-290 Mini Spray Dryer. Typical concentration of solids in feed solution was 2.5%. The spray drying was conducted with an inlet temperature of 120° C. and a pump rate of 3.6 ml/min. The make-up of each batch is set out in Table 1.

TABLE 1

| Batch No. | Paracetamol (wt %) | HPMC (wt %) | SDS (wt %) | Tween 80 (wt %) | Pluronic F-127 (wt %) | Mannitol (wt %) |
|---|---|---|---|---|---|---|
| 1 | 50 | 40 | 1 | — | — | 0 |
| 2 | 50 | — | 1 | — | — | 49 |
| 3 | 50.3 | 20.1 | — | 0.5 | — | 29.1 |
| 4 | 50.0 | 20 | — | — | 1 | 29.0 |
| 5 | 70 | — | 1 | — | — | 29 |
| 6 | 80 | — | 1 | — | — | 19 |
| 7 | 90 | — | 1 | — | — | 9 |

In order to measure the paracetamol particle size distribution (PSD), a 0.5 g sample of the spray dried paracetamol batches was dissolved into 30 ml 0.1 mol/l hydrochloride acid (HCl) solution with stirring (magnetic bar) for 10 minutes before measurements were taken using Malvern Nano-S particle sizer. The dispersions were corrected for viscosity.

To study the dissolution characterization, a 1.0 g sample (equivalent to 500 mg paracetamol) of the spray dried paracetamol batches was dissolved into 1000 ml of 0.1 M HCl at 37° C. with overhead paddle stirring at 50 rpm. Aliquots of each solution were taken at 1, 5, and 10 minutes. The dispersions were then diluted with 0.1 M HCl solution for UV characterization. The dissolution is expressed as a percentage of the initial paracetamol concentration that has dissolved after specific time intervals, for each formulation.

TABLE 2

| Batch No. | PSD (nm) | Dissolution in 0.1M HCl (1 min) | Dissolution in 0.1M HCl (5 min) |
|---|---|---|---|
| 1 | 230 | 48 | 78 |
| 2 | 145 | 92 | 99 |
| 3 | 323 | 95 | 99 |
| 4 | 310 | 96 | 99 |
| 5 | — | 72 | 99 |
| 6 | — | 62 | 95 |
| 7 | — | 45 | 93 |

PSD not determined for batch nos. 5, 6 or 7 as multi-modal distributions were obtained.

A UV calibration curve was also obtained by dissolving different amounts of paracetamol into 0.1 M HCl solution.

Table 3 lists the featured XRD diffraction values for different paracetamol samples. The first column (Para) is for untreated paracetamol crystals, the second column (Para-22) is for spray dried paracetamol sample, the third column (Para-22-Blank) is for spray dried 'blank' sample without paracetamol, and the fourth column (Para-22-Blended) is for a mechanically blended sample with paracetamol. Values in bold are for the featured XRD diffraction pattern from paracetamol.

TABLE 3

| Para-Crystals | Para-22 | Para-22-Blank | Para-22-Blended |
|---|---|---|---|
|  | 9.12 | 9.33 | 8.5 |
|  | 8 | 8.05 |  |
| 7.25 | 7.25 |  | 7.25 |
| 6.4 | 6.4 | 6.4 | 6.4 |
|  |  |  | 6 |
| 5.65 | 5.65 |  | 5.62 |
| 5.28 | 5.26 |  | 5.27 |
|  | 5.1 | 5.1 |  |
| 4.85 | 4.85 |  | 4.86 |
|  | 4.72 | 4.7 | 4.7 |
|  | 4.47 | 4.47 | 4.63 |
| 4.36 | 4.32 | 4.33 | 4.34 |
| 4.26 | 4.15 | 4.15 | 4.2 |
|  | 4.0 |  | 4.0 |
| 3.86 |  |  | 3.84 |
| 3.78 | 3.77 |  | 3.78 |
| 3.65 | 3.65 |  | 3.64 |
| 3.6 | 3.52 | 3.52 | 3.43 |
| 3.35 | 3.35 |  | 3.35 |
| 3.28 | 3.28 | 3.3 | 3.27 |
| 3.2 | 3.2 | 3.22 | 3.19 |
| 3.13 | 3.16 | 3.16 | 3.15 |
|  |  |  | 3.08 |
| 3.05 | 3.05 |  | 3.05 |

The data in Table 3 shows that the nano-particles of paracetamol prepared by the single phases process described above are completely crystalline with no amorphous content and that they retain essentially the same crystallinity and crystal form as the starting paracetamol compound.

Example 17

Ibuprofen

This example summarises the experimental conditions used to produce a spray dried ibuprofen formulation.

The following materials were used as purchased, without further purification:
Ibuprofen (Mw 206.29, Aldrich)
Polyvinylalcohol (PVA, Mw 13,000-23,000, 98% hydrolysed, Aldrich)
Hydroxypropyl methyl cellulose (HPMC, Mw 10,000, Aldrich)
Tween 40 (Aldrich)
Plutonic F-127 (Sigma)

For each formulation, ibuprofen was dissolved into ethanol (15 ml) and the other excipients were dissolved into distilled water (10 ml). The aqueous solution and the ethanol solution were mixed together to give a clear solution with a solids content of 4%. The solution was spray dried (BUCHI mini spray dryer B-290) at 120° C. with liquid feed rate at 2.5 ml/min. A white powder was obtained and was collected in a sample vial for analysis.

Powdered samples were added to deionised water at a concentration of 5% of ibuprofen. The dispersions were stirred (magnetic bar) for 10 minutes before measurements were taken using Malvern Nano-S particle sizer. The dispersions were corrected for viscosity. The make-up and particle size distributions of the samples are set out in Table 4.

TABLE 4

| Sample Name | Ibuprofen (wt %) | PVA (wt %) | HPMC (wt %) | Pluronic F-127 (wt %) | Tween 40 (wt %) | PSD (nm) |
| --- | --- | --- | --- | --- | --- | --- |
| 1 | 15 | 85 | — | — | — | 23 |
| 2 | 30 | — | 70 | — | — | 18 |
| 3 | 30 | 55 | — | 15 | — | 51 |
| 4 | 30 | — | 55 | — | 15 | 177 |

Example 18

Aspirin

The following materials were used as purchased, without further purification:
Aspirin (Mw 180.16, Aldrich)
Polyvinylalcohol (PVA, Mw 9,000-10,000, 80% hydrolysed, Aldrich)
Hydroxypropyl methyl cellulose (HPMC, Mw 10,000, Aldrich)
Tween 80 (Aldrich)
Sodium dodecylsulphate (SDS, 98%, Mw 288.18, BDH)
Mannitol (Mw 182.17, Aldrich)

Powdered samples were added to deionised water at the concentrations shown below. The dispersions were stirred (magnetic bar) for 10 minutes before measurements were taken using Malvern Nano-S particle sizer. The dispersions were corrected for viscosity.

Emulsion Procedure

PVA (0.45 g) and SDS (1.0 g) were dissolved in water (24 ml) with stirring using and overhead paddle stirrer. In a separate flask aspirin (0.4 g) was dissolved in chloroform (24 ml) and the resulting solution was added dropwise to the stirred aqueous solution. The emulsion that formed was then homogenised at 20,500 rpm for 2 minutes followed by 24,000 rpm for 2 minutes and then was spray-dried (BUCHI mini spray dryer B-290) at 130° C. with liquid feed rate at 3.6 ml/min. A white powder was obtained and was collected in a sample vial for analysis. This material had a particle size (Zave) of 82 nm measured at 4 mg/ml of sample.

Single Phase Procedure (See Table 5)

For each formulation, aspirin was dissolved into acetone and the other excipients were dissolved into distilled water. The aqueous solution and the acetone solution were mixed together to give a clear solution with a solids content shown in the table. The solution was spray dried (BUCHI mini spray dryer B-290) at 100° C. with liquid feed rate at 3.6 ml/min. A white powder was obtained and was collected in a sample vial for analysis. The particle size measurement was carried out at a concentration of 2.4 mg/ml in all cases.

TABLE 5

| Sample Name | Aspirin (wt %) | HPMC (wt %) | Mannitol (wt %) | SDS (wt %) | Tween 80 (wt %) | Water:Acetone | % Solids | PSD (nm) |
| --- | --- | --- | --- | --- | --- | --- | --- | --- |
| 1 | 85 | — | 5 | — | 10 | 1.1:1 | 1.4 | 20 |
| 2 | 85 | 5 | 5 | — | 5 | 1:1.45 | 1.7 | 53 |
| 3 | 85 | 7.5 | 7.5 | — | — | 1:1.5 | 3 | 129 |

The invention claimed is:

1. A process for the production of a substantially solvent-free, water-soluble composition in powder form, the composition consisting of solid powder particles, wherein each particle consists of a water-soluble carrier material in which nanoparticles of a water-insoluble paracetamol or NSAID are dispersed, which process comprises the steps of:
   a) providing an emulsion consisting of:
      i) a solution of a water-insoluble paracetamol or NSAID in a water-immiscible solvent for the same, and
      ii) an aqueous solution of a water-soluble carrier material in water,
   b) spray-drying the emulsion to remove each solvent to thereby obtain said powdered composition of solid powder particles,
      wherein the particle size of the water-insoluble paracetamol or NSAID particles comprised in the solid powder particles obtained in step (b), as measured when said powdered composition is stirred using a magnetic bar into water whereupon the water-soluble carrier material dissolves and the water-insoluble paracetamol or NSAID particles disperse through the water, is below 1000 nm, and
   wherein the water-soluble carrier material consists of a polymer and/or a surfactant, said polymer being chosen from the group consisting of: polyethylene glycol, polyvinylpyrrolidone, poly(2-ethyl-2-oxazaline), polyvinyl alcohol, hydroxypropyl cellulose, hydroxypropyl methylcellulose and alginate.

2. The process according to claim 1, wherein the spray drying process is conducted at a temperature at or above 120° C.

3. The process according to claim 1, wherein the carrier material includes at least one of alkoxylated non-ionic surfactant, ether sulphate surfactant, cationic surfactant or ester surfactant.

4. The process according to claim 1, wherein the water-immiscible solvent includes at least one of dichloromethane and chloroform.

5. A process for the preparation of a medicament for use in the treatment of pain, which comprises the step of preparing a composition by a process according to claim 1.

* * * * *